US011950764B2

(12) United States Patent
Wang et al.

(10) Patent No.: US 11,950,764 B2
(45) Date of Patent: Apr. 9, 2024

(54) WIRE FIXING STRUCTURE AND ENDOSCOPE

(71) Applicant: OLYMPUS CORPORATION, Tokyo (JP)

(72) Inventors: Xiongwei Wang, Hino (JP); Tsukasa Ota, Hachioji (JP); Takuto Yoshinaga, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 744 days.

(21) Appl. No.: 17/096,247

(22) Filed: Nov. 12, 2020

(65) Prior Publication Data

US 2021/0059506 A1 Mar. 4, 2021

Related U.S. Application Data

(63) Continuation of application No. PCT/JP2019/006311, filed on Feb. 20, 2019.

(30) Foreign Application Priority Data

Jun. 28, 2018 (JP) .................................. 2018-122871

(51) Int. Cl.
*A61B 1/005* (2006.01)
*A61B 1/00* (2006.01)

(52) U.S. Cl.
CPC ............ *A61B 1/0057* (2013.01); *A61B 1/005* (2013.01); *A61B 1/0051* (2013.01); *A61B 1/0052* (2013.01); *A61B 1/00098* (2013.01)

(58) Field of Classification Search
CPC ...... A61B 1/005–0057; A61B 1/00066; A61B 2017/003; A61B 2017/00318;

(Continued)

(56) References Cited

U.S. PATENT DOCUMENTS 4,941,454 A * 7/1990 Wood ................... A61B 1/0016
600/152
5,569,157 A 10/1996 Nakazawa et al.
(Continued)

FOREIGN PATENT DOCUMENTS

JP 4-124103 U 11/1992
JP 4-367643 A 12/1992
(Continued)

OTHER PUBLICATIONS

International Search Report dated May 21, 2019 received in International Application No. PCT/JP2019/006311, together with an English-language translation.

*Primary Examiner* — Ryan N Henderson
*Assistant Examiner* — Pamela F Wu
(74) *Attorney, Agent, or Firm* — Scully, Scott, Murphy & Presser, P.C.

(57) ABSTRACT

A wire fixing structure includes: a first hole portion through which a wire passes; and a second hole portion which is formed in a direction orthogonal to the first hole portion and communicates with the first hole portion. The wire includes: a first portion which is inserted into and is disposed in the first hole portion; a second portion which is extended from the first hole portion and wound around the outer peripheral portion of a wire fixing member; and a third portion which is inserted into and is disposed in the first hole portion again after the second portion is wound around the outer peripheral portion. The fastening member is inserted into the second hole portion and fixes the first portion and the third portion by pressing in the first hole portion.

20 Claims, 9 Drawing Sheets

(58) Field of Classification Search
CPC ........... A61B 2017/00323; A61B 2017/00327; G02B 23/2476; A61M 25/0133; A61M 25/0136; A61M 25/0147; A61M 2025/015
USPC .................................................. 600/146–150
See application file for complete search history.

(56) References Cited

U.S. PATENT DOCUMENTS

| | | |
|---|---|---|
| 5,707,344 A | 1/1998 | Nakazawa et al. |
| 2005/0054899 A1 | 3/2005 | Miyake |

FOREIGN PATENT DOCUMENTS

| | | |
|---|---|---|
| JP | 6-315460 A | 11/1994 |
| JP | 7-178041 A | 7/1995 |
| JP | 2004-350866 A | 12/2004 |

\* cited by examiner

WIRE FIXING STRUCTURE AND ENDOSCOPE

CROSS REFERENCE TO RELATED APPLICATION

This application is a continuation application of PCT/JP2019/006311 filed on Feb. 20, 2019 and claims benefit of Japanese Application No. 2018-122871 filed in Japan on Jun. 28, 2018, the entire contents of which are incorporated herein by this reference.

BACKGROUND OF THE INVENTION

1. Field of the Invention

The present invention relates to a wire fixing structure which fixes a wire for operating a bending portion provided in an insertion section, and an endoscope.

2. Description of the Related Art

The endoscope has an insertion section which is inserted into a lumen. The insertion section is formed in an elongated tubular shape corresponding to an observation object so as to cope with various observation objects. As such an insertion section of the endoscope, there has been known an insertion section which includes a bending portion for changing an observation direction of a field of view.

The bending portion of the endoscope is bent by rotatably operating an operation member such as a bending lever provided on the operation section. In the endoscope, a pulley which is connected to a bending lever and is rotatable is disposed in an operation section. A towing wire for operating the bending portion is wound around the pulley.

Such a configuration is disclosed in, for example, Japanese Patent Application Laid-Open Publication No. 7-178041. Japanese Patent Application Laid-Open Publication No. 7-178041 discloses a bending operation device of an endoscope where a towing wire which is a bending wire is inserted into a cylindrical collar fitted into a cutout portion of the pulley, and the collar which is a wire fixing member is fixed to the pulley by a screw.

SUMMARY OF THE INVENTION

According to an aspect of the present invention, a wire fixing structure includes: a wire provided for performing a bending operation of a bending portion of an endoscope; a wire fixing member mounted on a pulley which is configured to tow or slacken the wire by rotation, the wire fixing member including a first hole portion through which the wire passes and a second hole portion which communicates with the first hole portion in an intersecting manner; and a fastening member inserted into the second hole portion and fixing the wire disposed in the first hole portion by pressing, wherein the wire includes: a first portion which is inserted into and is disposed in the first hole portion; a second portion which is extended from the first hole portion; and a third portion which is inserted into and is disposed in the first hole portion again after the second portion is extended from the first hole portion, and the fastening member is inserted into the second hole portion and fixes the first portion and the third portion by pressing in the first hole portion.

According to another aspect of the present invention, an endoscope includes a wire fixing structure which includes: a wire provided for performing a bending operation of a bending portion of an endoscope; a wire fixing member mounted on a pulley which is configured to tow or slacken the wire by rotation, the wire fixing member including a first hole portion through which the wire passes and a second hole portion which communicates with the first hole portion in an intersecting manner; and a fastening member inserted into the second hole portion and fixing the wire disposed in the first hole portion by pressing, wherein the wire includes: a first portion which is inserted into and is disposed in the first hole portion; a second portion which is extended from the first hole portion; and a third portion which is inserted into and is disposed in the first hole portion again after the second portion is extended from the first hole portion, and the fastening member is inserted into the second hole portion and fixes the first portion and the third portion by pressing in the first hole portion.

DETAILED DESCRIPTION OF THE PREFERRED EMBODIMENT

Hereinafter, a preferred mode of the present invention is described with reference to drawings. In drawings used in the description made hereinafter, for the sake of setting sizes of respective components legible in the drawings, the scales of the respective components are made different from each other. The present invention is not limited to the number and the amounts of components described in the drawings, the shapes of the components, ratios between the sizes of the components, and the relative positional relationships among the components described in the drawings. Further, in the description made hereinafter, there are cases where the description is made by assuming upward and downward directions of the drawing when the drawing is viewed in a direction toward a sheet of paper on which the drawing is illustrated as an upper portion and a lower portion of a component.

First, an aspect of the present invention is described hereinafter with reference to the drawings.

A schematic configuration of an endoscope according to a first embodiment of the present invention is described hereinafter with reference to the drawings.

Figure 1:
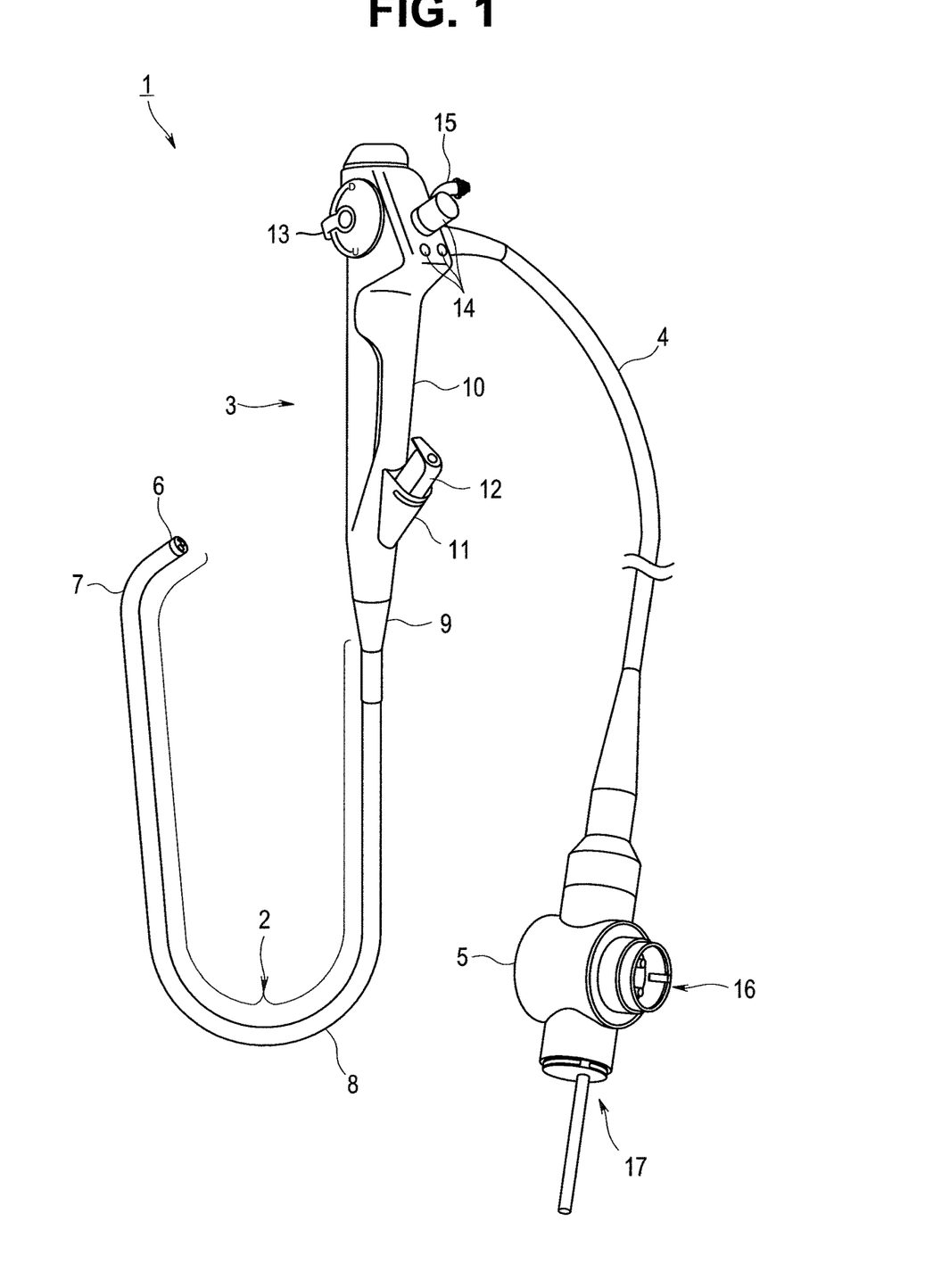
FIG. 1 is an overall perspective view showing a schematic configuration of an endoscope according to an aspect of the present invention.
Figure 2:
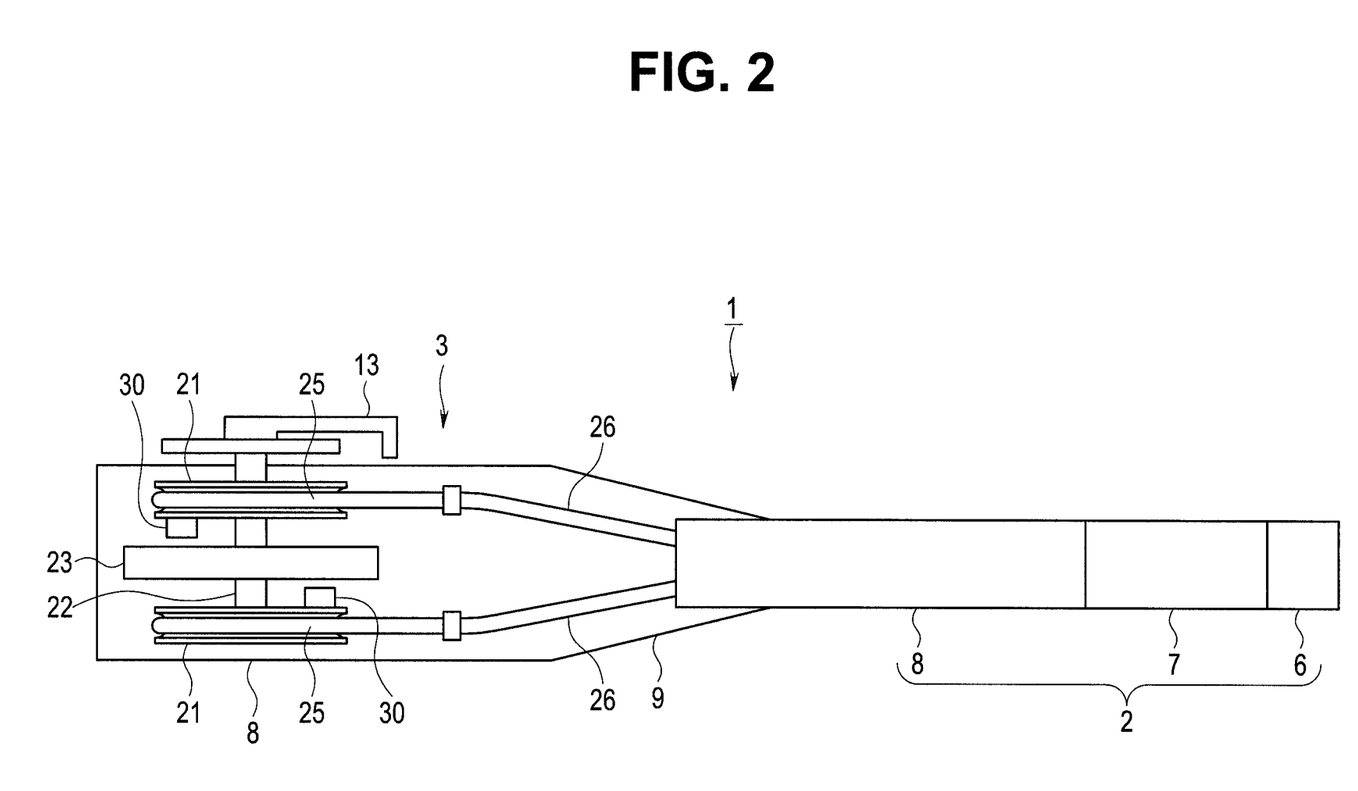
FIG. 2 is a schematic view of the endoscope according to the aspect of the present invention schematically showing an inside of an operation section.
Figure 3:
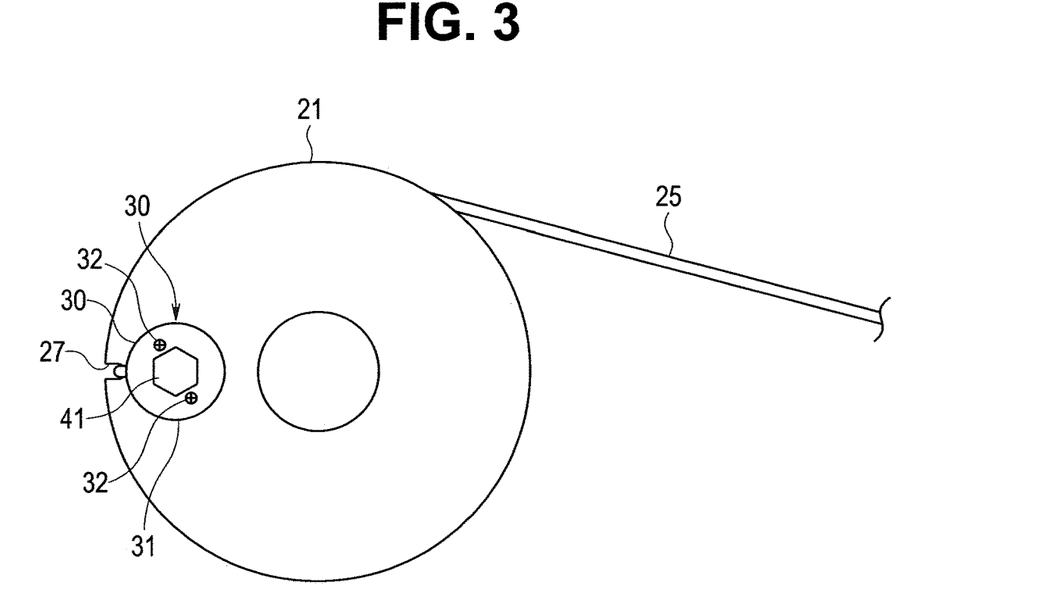
FIG. 3 is a side view showing a configuration of a pulley which includes a wire fixing structure according to the aspect of the present invention.
Figure 4:
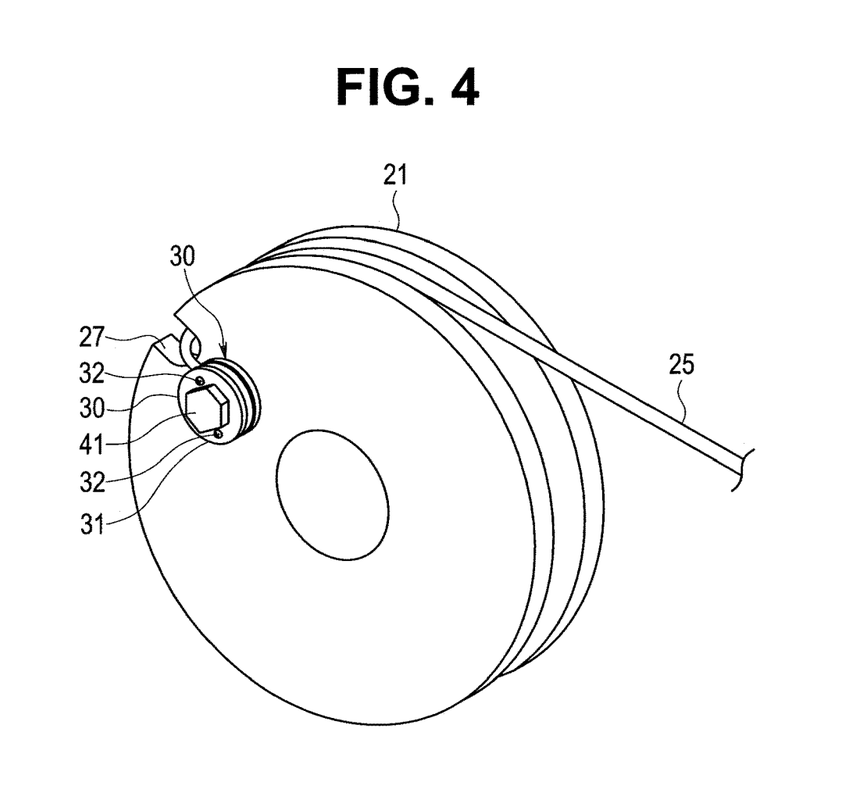
FIG. 4 is a perspective view showing the configuration of the pulley which includes the wire fixing structure according to the aspect of the present invention.
Figure 5:
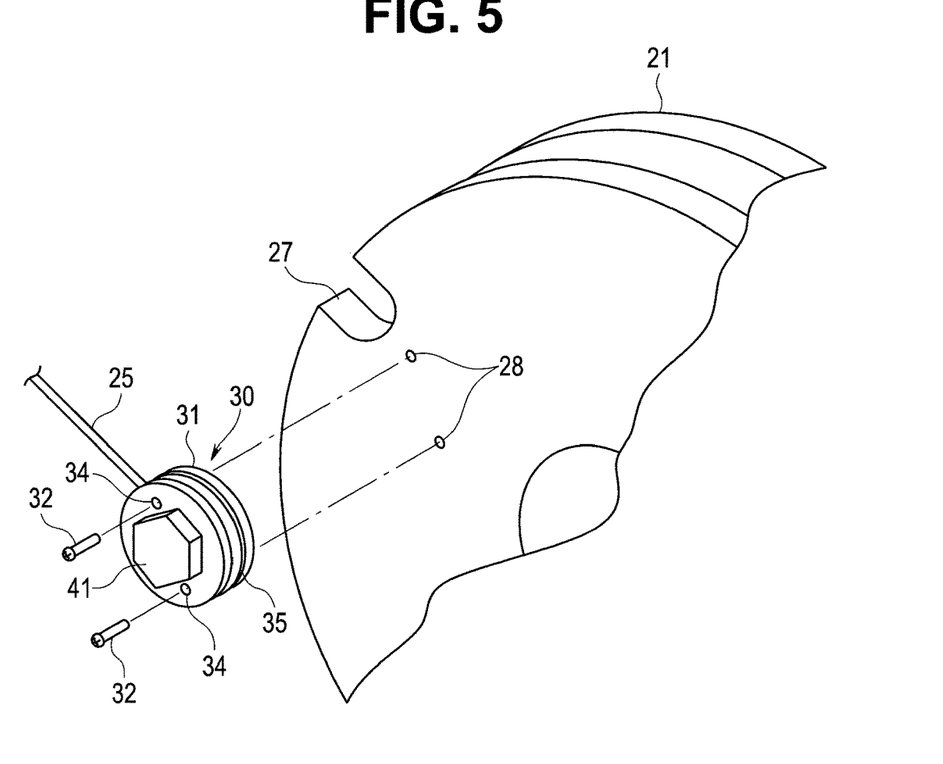
FIG. 5 is an exploded perspective view showing a configuration of the wire fixing structure according to the aspect of the present invention.
Figure 6:
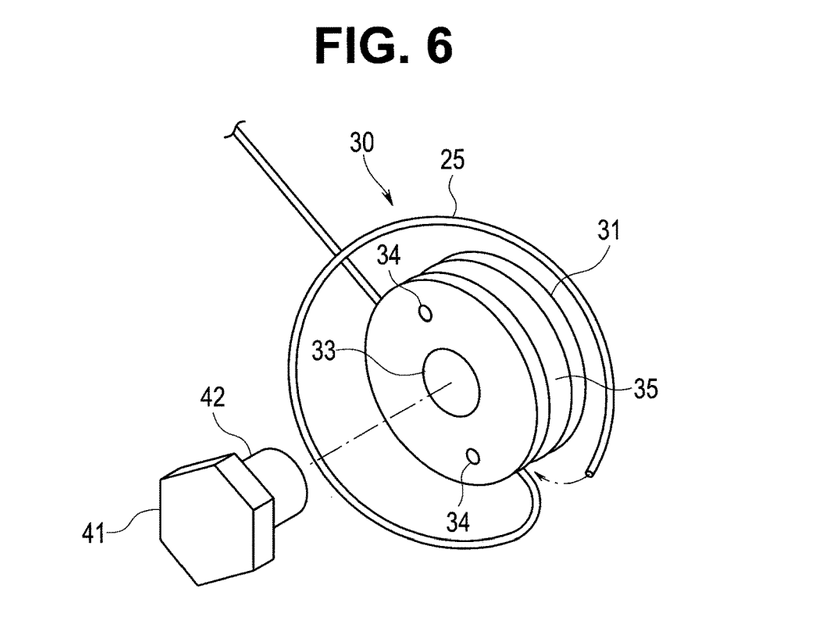
FIG. 6 is an exploded perspective view showing a state where the wire fixing structure according to the aspect of the present invention is fixed to the pulley.
Figure 7:
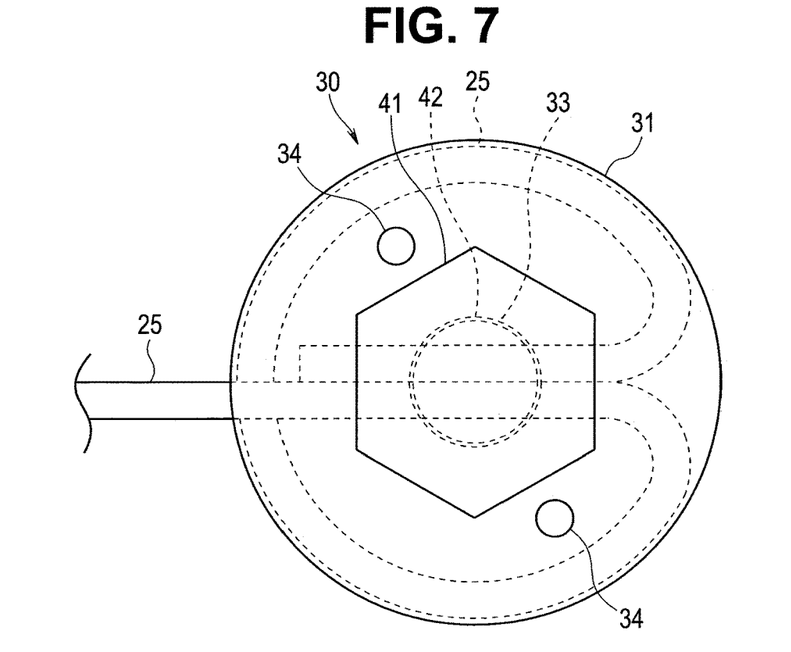
FIG. 7 is a side view showing the configuration of the wire fixing structure according to the aspect of the present invention.
Figure 8:
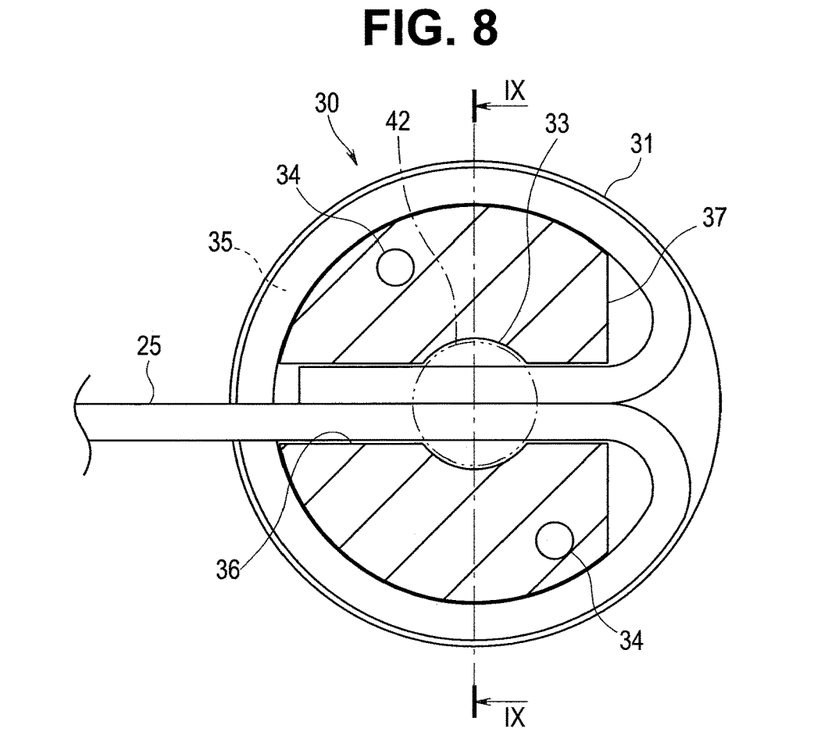
FIG. 8 is a cross-sectional view showing the configuration of the wire fixing structure according to the aspect of the present invention.
Figure 9:
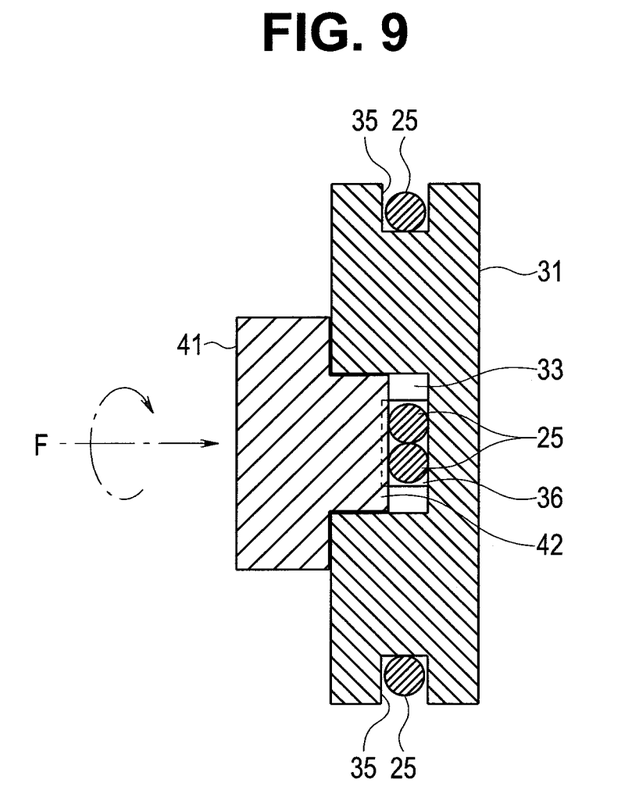
FIG. 9 is a cross-sectional view showing the configuration of the wire fixing structure according to the aspect of the present invention taken along a line IX-IX in FIG. 8.
Figure 10:
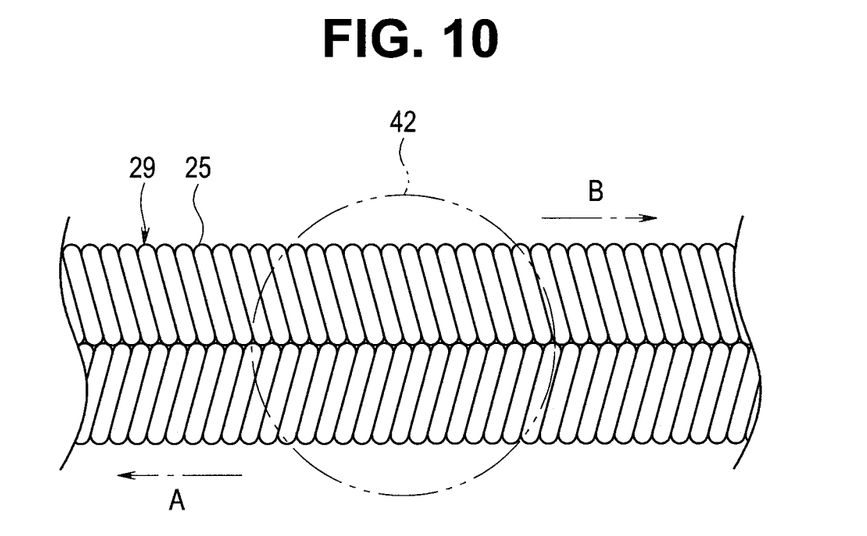
FIG. 10 is a view relating to the aspect of the present invention showing a fixed state of a bending wire which is a stranded wire.

FIG. 1 is an overall perspective view showing a schematic configuration of an endoscope according to an aspect of the present invention, FIG. 2 is a schematic view of the endoscope schematically showing an inside of an operation section, FIG. 3 is a side view showing a configuration of a pulley which includes a wire fixing structure, FIG. 4 is a perspective view showing the configuration of the pulley which includes the wire fixing structure, FIG. 5 is an exploded perspective view showing a configuration of the wire fixing structure, FIG. 6 is an exploded perspective view showing a state where the wire fixing structure is fixed to the pulley, FIG. 7 is a side view showing the configuration of the wire fixing structure, FIG. 8 is a cross-sectional view showing the configuration of the wire fixing structure, FIG. 9 is a cross-sectional view showing the configuration of the wire fixing structure taken along a line IX-IX in FIG. 8, and FIG. 10 is a view showing a fixed state of a bending wire which is a stranded wire.

As shown in FIG. 1, the endoscope 1 according to the first embodiment of the present invention is mainly constituted of: an insertion section 2, an operation section 3, a universal cord 4 and an endoscope connector 5 and the like.

The insertion section 2 is formed in an elongated shape, and is inserted into a subject. In the embodiment, the entirety of the insertion section 2 is formed of a multi-lumen tube. The insertion section 2 is formed by connecting a distal end portion 6, a bending portion 7 which is an endoscope bending portion, and a flexible tube portion 8 in order from a distal end side of the insertion section 2. The insertion section 2 has flexibility as a whole.

In the embodiment, the insertion section 2 is formed of a multi-lumen tube which can be manufactured at a low cost so that the insertion section 2 is of a type which can be used only once (disposable type).

An image pickup unit which is an image pickup apparatus in which an image pickup device and the like are disposed, an illumination optical system which irradiates an illumination light toward a front side and the like (none of these components shown) are incorporated in the distal end portion 6 of the insertion section 2.

A mode of the endoscope to which the present invention is applicable is not limited to the above-mentioned example (an electronic endoscope which includes an image pickup unit and the like). The present invention is applicable to modes other than the above-mentioned mode. For example, the present invention is applicable to a so-called fiberscope taking a mode where the fiberscope does not include an image pickup unit and an image guide fiber is disposed on the insertion section 2 or the like.

The bending portion 7 is configured such that when the bending portion 7 receives a rotary operation of a bending lever 13 for performing a bending operation among operation members mounted on the operation section 3, the bending portion 7 can be actively bent in a first direction and a second direction opposite to the first direction. In the embodiment, the bending portion 7 can be actively bent in two directions, that is, upward and downward directions (UP and DOWN). In this case, the upward and downward directions (UP and DOWN) are the upward and downward directions on an endoscope image which is picked up by the image pickup unit.

The bending directions of the bending portion 7 are not limited to two directions, that is, the upward and downward directions (UP and DOWN). The bending portion 7 may be configured to be actively bent in four directions, that is, upward, downward, leftward and rightward directions (UP, DOWN, LEFT and RIGHT).

The flexible tube portion 8 has flexibility such that the flexible tube portion 8 is passively flexible. In the flexible tube portion 8, besides a lumen for a treatment instrument insertion channel, the following lumens are formed. Such lumens are constituted of: a lumen which allows various signal lines extending from the image pickup unit incorporated in the distal end portion 6 to the inside of the universal cord 4 by way of the inside of the operation section 3 to pass through the lumen; and a lumen which allows a light guide (not shown) for guiding a light emitted from a light source device (not shown) which is external equipment to an illumination window (not shown) disposed on a distal end surface of the distal end portion 6 to pass through the lumen.

The light source may take a mode where a light emitting element (for example, a light emitting diode (LED)) is disposed in the operation section. In the light source having such a configuration, the light guide (not shown) is used for guiding a light emitted from the LED in the operation section to the illumination window disposed on the distal end portion 6.

As a mode different from the above-mentioned mode, the light source may take a mode where a light emitting element such as an LED is disposed in the distal end portion 6, for example, at a position close to a proximal end of the illumination window. In the light source having such a configuration, a light emitted from the LED directly passes through the illumination window and illuminates a front side of the distal end portion 6.

In other words, in such a configuration, it is unnecessary to dispose the light guide (not shown) in the flexible tube portion 8. On the other hand, it is necessary to make an electricity supply line for emitting the LED disposed in the distal end portion 6 or the like pass through the lumen in the flexible tube portion 8.

The operation section 3 is a configuration unit which is connected to a proximal end portion of the insertion section 2, and includes a plurality of operation members and the like. In other words, the operation section 3 includes a bend preventing portion 9, a grasping portion 10, the plurality of operation members (13, 14 and the like), a treatment instrument insertion portion 11, a suction valve 15 and the like.

The bend preventing portion 9 is disposed at a connecting portion between a distal end portion of the operation section 3 and a proximal end portion of the flexible tube portion 8, and covers the proximal end portion of the flexible tube portion 8. Accordingly, the bend preventing portion 9 is a protective member which prevents the flexible tube portion 8 from being inadvertently and suddenly broken when the endoscope 1 is used.

The grasping portion 10 is a housing portion which stores various configuration members in the grasping portion 10. The grasping portion 10 is connected to the bend preventing portion 9. The grasping portion 10 is a portion which a user grasps by holding in his/her hand when the endoscope 1 is used.

The plurality of operation members are disposed on an outer surface of the grasping portion 10, and are members for operating various functions of the endoscope 1. The plurality of operation members include, for example, besides the bending lever 13 for performing bending operations in the upward and downward directions of the bending portion 7, an operation member for performing an air/water feeding operation and a suction operation, the operation member 14 for performing operations each corresponding to the image pickup unit and the illumination unit and the like.

The treatment instrument insertion portion 11 is a configuration portion which has a treatment instrument insertion opening (not shown) into which various treatment instruments (not shown) are inserted, and includes a treatment instrument insertion path which communicates with the treatment instrument insertion channel in the operation section 3.

A forceps plug 12 is disposed in the treatment instrument insertion portion 11. The forceps plug 12 is a lid member which opens or closes the treatment instrument insertion opening, and is configured to be detachably (exchangeably) mounted on the treatment instrument insertion portion 11. The suction valve 15 is a connecting portion to which a suction conduit is connected. The suction conduit is connected to a suction device not shown.

The universal cord 4 is hollow tumbler member which has flexibility and extends from the operation section 3. The universal cord 4 is a composite cable through which various signal lines, a light guide (not shown), and a tube for air/water feeding and the like pass. The various signal lines pass through the inside of the insertion section 2 from the distal end portion 6 of the insertion section 2, and extend through the inside of the operation section 3. The light guide is extended from the light source device (not shown) which is the external equipment. The tube for air/water feeding is extended from an air/water feeding device (not shown) which is external equipment.

The endoscope connector 5 is a connecting member which is disposed on a distal end portion of the universal cord 4, and ensures the connection between external equipment and the endoscope 1. An electric connector portion 16 is mounted on a side surface portion of the endoscope connector 5. A video processor (not shown) which is external equipment is connected to the electric connector portion 16 by a signal cable.

The endoscope connector 5 includes a light source connector portion 17 and the like. A light guide bundle which is connected to a light source device (not shown) which is an external device and an electric cable (not shown) which is a bundle of the above-mentioned respective signal lines are connected to the light source connector portion 17.

As shown in FIG. 2, in the operation section 3, two pulleys 21 are rotatably disposed about a shaft 22. The shaft 22 is connected to the bending lever 13 mounted on the operation section 3, and is pivotally supported on a bearing member 23 fixed in the operation section 3.

Bending wires 25 which are towing wires are wound around the two pulleys 21. The bending wires 25 pass through coil tubes 26, and are disposed in the insertion section 2 from the operation section 3. Wire fixing structures 30 described later which fix the respective bending wires 25 are disposed in the two pulleys 21.

Two bending wires 25 are connected to bending pieces or the like not shown which are disposed in the bending portion 7 of the insertion section 2. The two pulleys 21 rotate about the shaft 22 in an interlocking manner with a rotary operation of the bending lever 13.

With such an operation, the two bending wires 25 are towed or slackened so that the bending portion 7 is actively bent in two directions, that is, the upward and downward directions (UP and DOWN). A structure of the bending portion 7 is well known and hence, a detailed description of members which constitute the bending portion 7 and the like is omitted.

Next, the wire fixing structure 30 according to the embodiment is described in detail hereinafter.

In the endoscope 1, as shown in FIG. 3 and FIG. 4, the wire fixing structures 30 which fix end portions of the bending wires 25 are disposed on the respective side surfaces of the two pulleys 21 disposed in the operation section 3.

The wire fixing structure 30 includes: a fixing member 31 which fixes a wire having an approximately circular columnar shape; and a bolt 41 which is a wire pressing member functioning as a fastening member which is threadedly engaged with the fixing member 31.

As shown in FIG. 5, two hole portions 34 which penetrate side surfaces of the fixing member 31 are formed in the fixing member 31. Screws 32 are respectively inserted into the two hole portions 34.

The two screws 32 are threadedly mounted on two screw holes 28 formed in the side surface of the pulley 21. With such a configuration, the fixing member 31 is fixed to the side surface of the pulley 21.

A cutout portion 27 is formed in a portion of an outer peripheral portion of the side surface of the pulley 21 to which the fixing member 31 is fixed. The bending wire 25 having an end portion fixed to the fixing member 31 is engaged and wound around the outer peripheral portion of the pulley 21 along the cutout portion 27 of the pulley 21.

A detail of the wire fixing structure 30 which fixes the end portion of the bending wire 25 to the fixing member 31 is described hereinafter.

As shown in FIG. 6, one end portion of the bending wire 25 passes through the fixing member 31, is wound around one turn along a peripheral groove 35 formed on an outer peripheral portion of the fixing member 31 in a state where a tension is applied to the bending wire 25 and then, the bending wire 25 is inserted into the fixing member 31 again.

Then, as shown in FIG. 7, a male threaded portion 42 of the bolt 41 is threadedly engaged with a female threaded hole portion 33 having a threaded groove formed at an approximately center portion of the fixing member 31, and the bolt 41 which is a fixing screw is fastened.

As shown in FIG. 8, a through hole portion 36 which penetrates an outer peripheral portion of the fixing member 31 linearly in an outer peripheral direction is formed in the fixing member 31. The through hole portion 36 is formed such that the through hole portion 36 penetrates the center portion of the fixing member 31, and communicate with the female threaded hole portion 33 formed in a direction orthogonal to the through hole portion 36.

A deep groove 37 having a shape formed by linearly cutting out the peripheral groove 35 opposite to a direction that the bending wire 25 is extended is formed in the fixing member 31. The deep groove 37 is formed so as to facilitate winding the bending wire 25 around the peripheral groove 35, and bending and inserting the bending wire 25 into the through hole portion 36 again.

In this manner, one bending wire 25 is inserted into the through hole portion 36 of the fixing member 31, the bending wire 25 is wound around the outer peripheral portion of the fixing member 31 along the peripheral groove 35 one turn, and an end portion of the bending wire 25 is inserted into the through hole portion 36.

In other words, a portion of the bending wire 25 is inserted into and is disposed in the through hole portion 36 of the fixing member 31 thus forming a first portion. A portion of the bending wire 25 on an end portion side with respect to the first portion is extended from the through hole portion 36, and is wound around the outer peripheral portion of the fixing member 31 thus forming a second portion. After the second portion is wound around the fixing member 31, the end portion of the bending wire 25 is inserted into and is disposed in the through hole portion 36 again thus forming a third portion.

Accordingly, a state is brought about where an intermediate portion and the end portion of one bending wire 25 are juxtaposed in the through hole portion 36. Then, by threadedly engaging and fastening the male threaded portion 42 of the bolt 41 with the female threaded hole portion 33, the one bending wire 25 where the intermediate portion and the end portion are juxtaposed in the through hole portion 36 is pressed so that the bending wire 25 is fixed to the fixing member 31.

Accordingly, when the bolt 41 is inserted into and is threadedly mounted on the female threaded hole portion 33, the first portion and the third portion of the bending wire 25 disposed in the through hole portion 36 are pressed and fixed in the through hole portion 36.

In other words, as shown in FIG. 9, by fastening the bolt 41, a large friction is generated between the bending wire 25 which is inserted into the through hole portion 36 of the fixing member 31 and a hole wall which forms the through hole portion 36 by a pressing force F from an end surface of the male threaded portion 42 and hence, the bending wire 25 is strongly fixed to the fixing member 31.

As shown in FIG. 10, with a use of a stranded wire, a tension in an A direction in the drawing is generated at one side in the through hole portion 36. Accordingly, even when the other side of the bending wire 25 is pulled in a B direction opposite to the A direction, spiral concave and convex portions 29 formed on the outer periphery of the bending wire 25 mesh with each other and hence, slackening of the bending wire 25 is prevented.

In this manner, the wire fixing structure 30 of the embodiment is configured such that one bending wire 25 is wound around the outer periphery of the fixing member 31 one turn with a tension, and the bending wire 25 is fastened by the bolt 41 in the through hole portion 36 through which the intermediate portion and the end portion of the bending wire 25 pass, and hence, a fixing strength to fix the bending wire 25 to the fixing member 31 can be increased.

In other words, by fixing the bending wire 25 to the fixing member 31 in a winding manner, a larger friction force is generated, and the bending wire 25 is minimally slackened because of such a friction force and a fixing force by threaded fixing which presses two portions of the bending wire 25 in the through hole portion 36 by the bolt 41.

As described above, the endoscope 1 according to the embodiment includes the wire fixing structure 30 which can stably fix the bending wire 25 which is a towing wire for bending the bending portion 7 of the insertion section 2 to the pulley 21 without causing slackening of the bending wire 25.

(First Modification)

Figure 11:
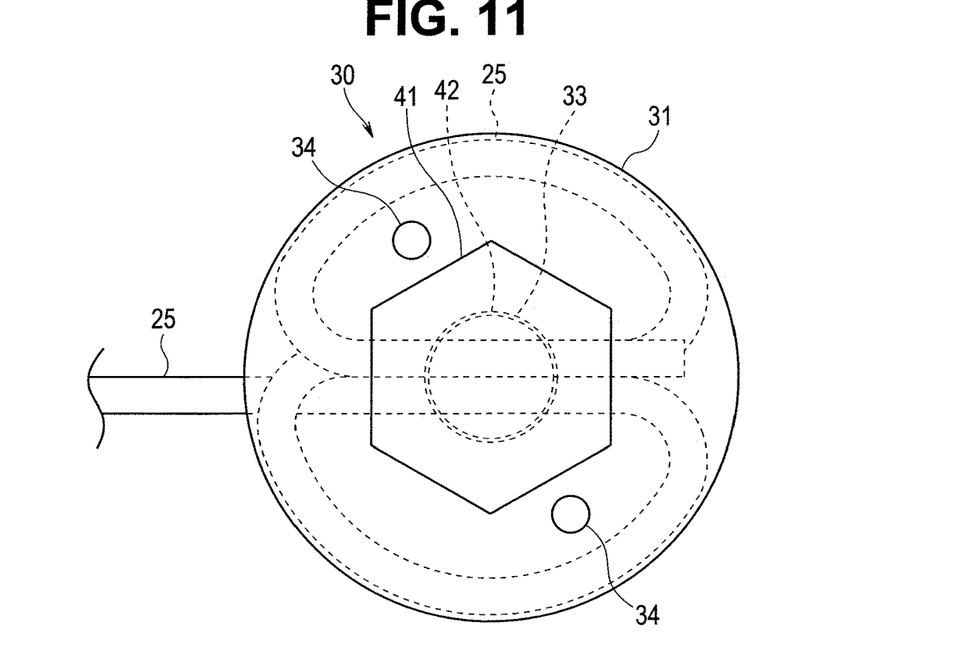
FIG. 11 is a side view showing a configuration of a wire fixing structure according to a first modification.

FIG. 11 is a side view showing a configuration of a wire fixing structure according to a first modification.

As shown FIG. 11, a bending wire 25 may be wound around a fixing member 31 in a figure eight shape.

In such a configuration, the bending wire 25 is inserted into a through hole portion 36 of the fixing member 31, is wound around an outer periphery of the fixing member 31 half turn on one side of the outer periphery along a peripheral groove 35 of the fixing member 31 and, again, is inserted into the through hole portion 36. Then, the bending wire 25 is wound around the outer periphery of the fixing member 31 half turn on the other side of the outer periphery along the peripheral groove 35 of the fixing member 31, and an end portion of the bending wire 25 is inserted into the through hole portion 36.

In the modification, a portion of the bending wire 25 is inserted into and is disposed in the through hole portion 36 of the fixing member 31 thus forming a first portion. A portion of the bending wire 25 on an end portion side with respect to the first portion is extended from the through hole portion 36, and is wound around a half of the outer peripheral portion of the fixing member 31 on one side thus forming a second portion. After the second portion is wound around the fixing member 31, a portion of the bending wire 25 is inserted into and is disposed in the through hole portion 36 again thus forming a third portion.

Then, a portion of the bending wire 25 on the end portion side with respect to the third portion is extended from the through hole portion 36, and is wound around a half of the outer peripheral portion of the fixing member 31 on the other side thus forming a fourth portion. After the fourth portion is wound around the fixing member 31, the end portion of the bending wire 25 is inserted into and is disposed in the through hole portion 36 again thus forming a fifth portion.

A bolt 41 is inserted into and is threadedly mounted on a female threaded hole portion 33, and the first portion, the third portion and the fifth portion of the bending wire 25 disposed in the through hole portion 36 are pressed and fixed in the through hole portion 36.

With such a configuration, three portions of the bending wire 25 pass through the through hole portion 36 of the fixing member 31, and the three portions are fastened by the bolt 41 and hence, the bending wire 25 can be fixed to the fixing member 31 more strongly.

(Second Modification)

Figure 12:
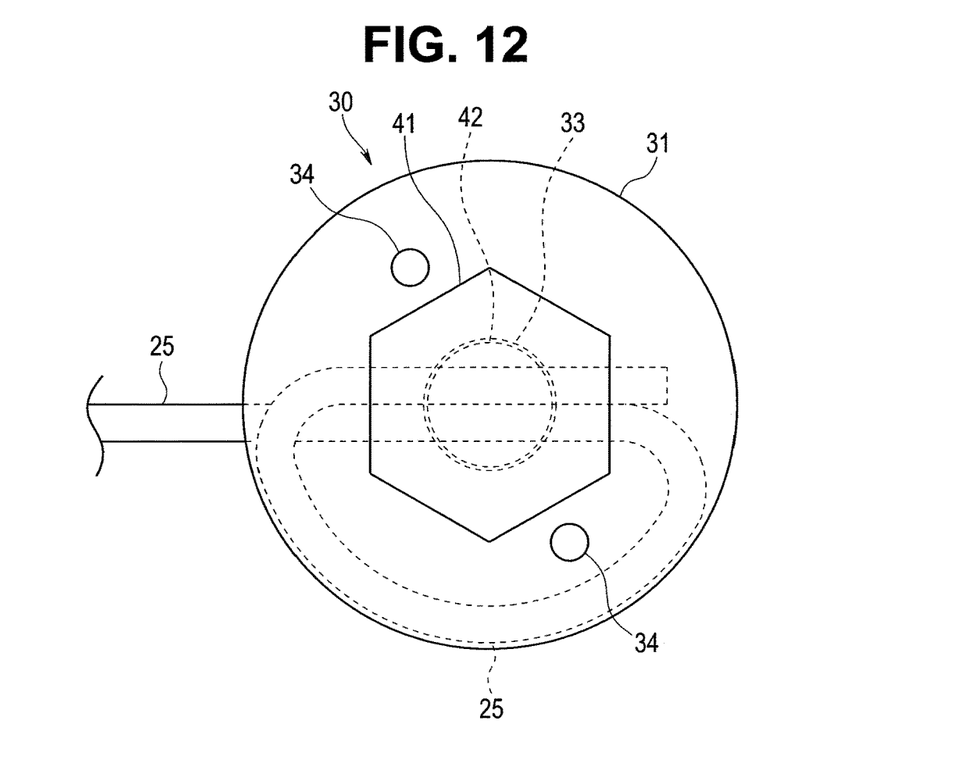
FIG. 12 is a side view showing a configuration of a wire fixing structure according to a second modification.

FIG. 12 is a side view showing a configuration of a wire fixing structure according to a second modification.

As shown in FIG. 12, a bending wire 25 may be wound around an outer periphery of the fixing member 31 half turn on one side of the outer periphery. Also in this case, in the same manner as the above-mentioned embodiment, two portions of the bending wire 25 pass through a through hole portion 36 of the fixing member 31, and the two portions are fastened by a bolt 41.

(Third Modification)

Figure 13:
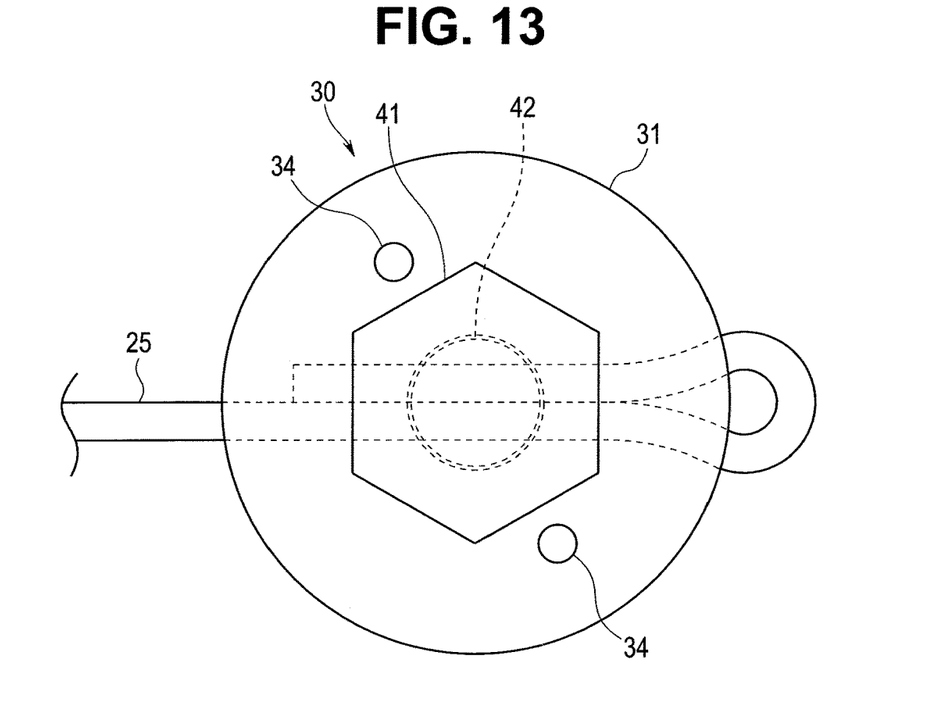
FIG. 13 is a side view showing a configuration of a wire fixing structure according to a third modification.

FIG. 13 is a side view showing a configuration of a wire fixing structure according to a third modification.

As shown in FIG. 13, a bending wire 25 is inserted into a through hole portion 36 of a fixing member 31, is folded back, and an end portion of the bending wire 25 is inserted into and is fixed to the through hole portion 36. Also in this case, in the same manner as the above-mentioned embodiment and the second modification, two portions of the bending wire 25 pass through the through hole portion 36 of the fixing member 31, and the two portions are fastened by a bolt 41.

(Fourth Modification)

Figure 14:
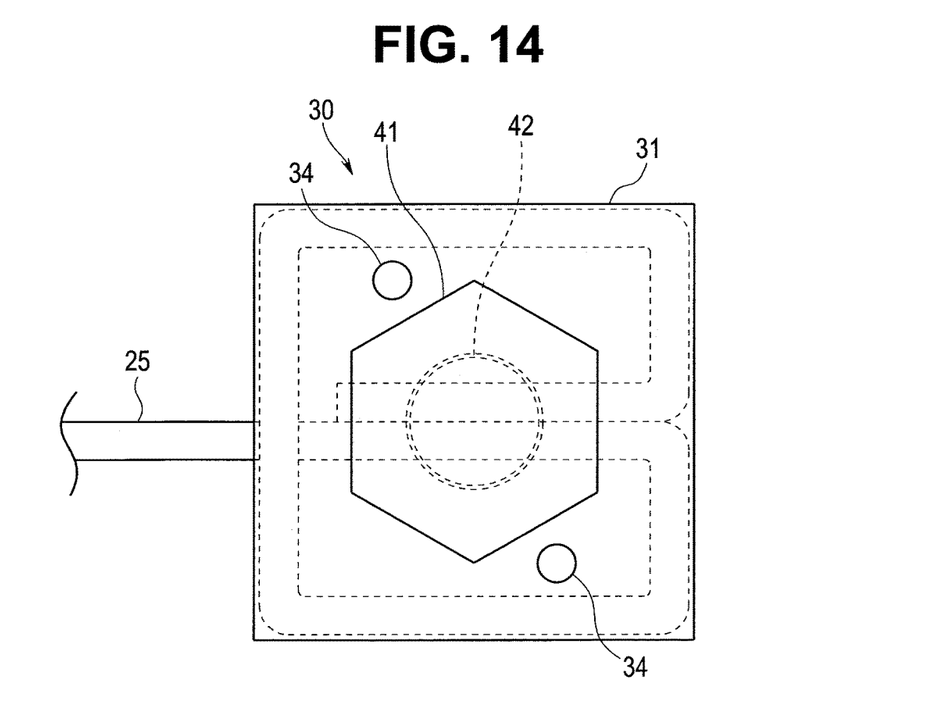
FIG. 14 is a side view showing a configuration of a wire fixing structure according to a fourth modification.

FIG. 14 is a side view showing a configuration of a wire fixing structure according to a fourth modification.

A fixing member 31 is not limited to a circular columnar shape, and the fixing member 31 may be formed in a polygonal shape where a cross section is non-circular. For example, the fixing member 31 may be formed in a quadrangular columnar shape where a cross section is a quadrangular shape as shown in FIG. 14. In this case, a bending wire 25 is bent at four corner portions of the fixing member 31 so that a larger friction force is generated and hence, the bending wire 25 can be strongly fixed to the fixing member 31.

(Fifth Modification)

Figure 15:
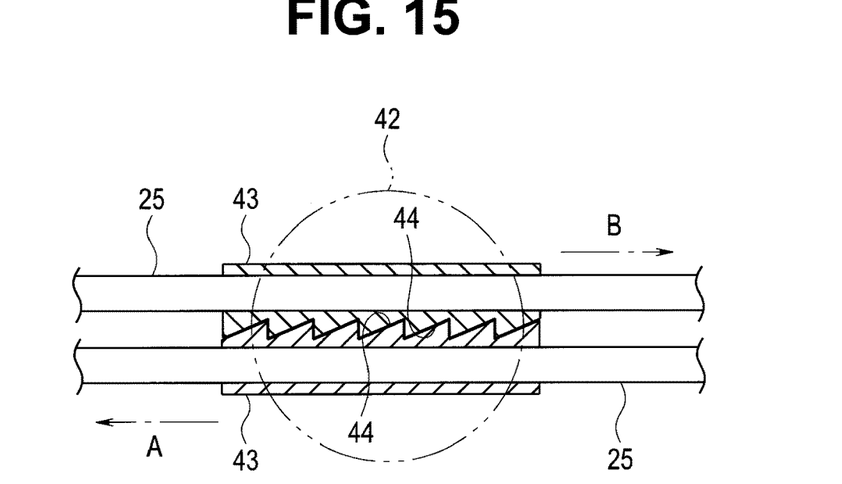
FIG. 15 is a partial cross-sectional view relating to a fifth modification showing a configuration where an anchor member is provided to a bending wire.

FIG. 15 a partial cross-sectional view showing a configuration where an anchor member is provided to a bending wire according to a fifth modification.

As shown in FIG. 15, two anchor members 43 each having a concave and convex portions 44 are provided to a bending wire 25.

The two anchor members 43 are disposed in a through hole portion 36 of a fixing member 31. Even when a tension in a direction A in the drawing is generated on the bending wire 25 on one side in the through hole portion 36 and the bending wire 25 on the other side is pulled in a direction B on an opposite side, the concave and convex portions 44 formed in the anchor members 43 mesh with each other and are locked to each other thus preventing slackening of the bending wire 25.

The two anchor members 43 are fastened by a bolt 41 in the through hole portion 36 of the fixing member 31.

(Sixth Modification)

Figure 16:
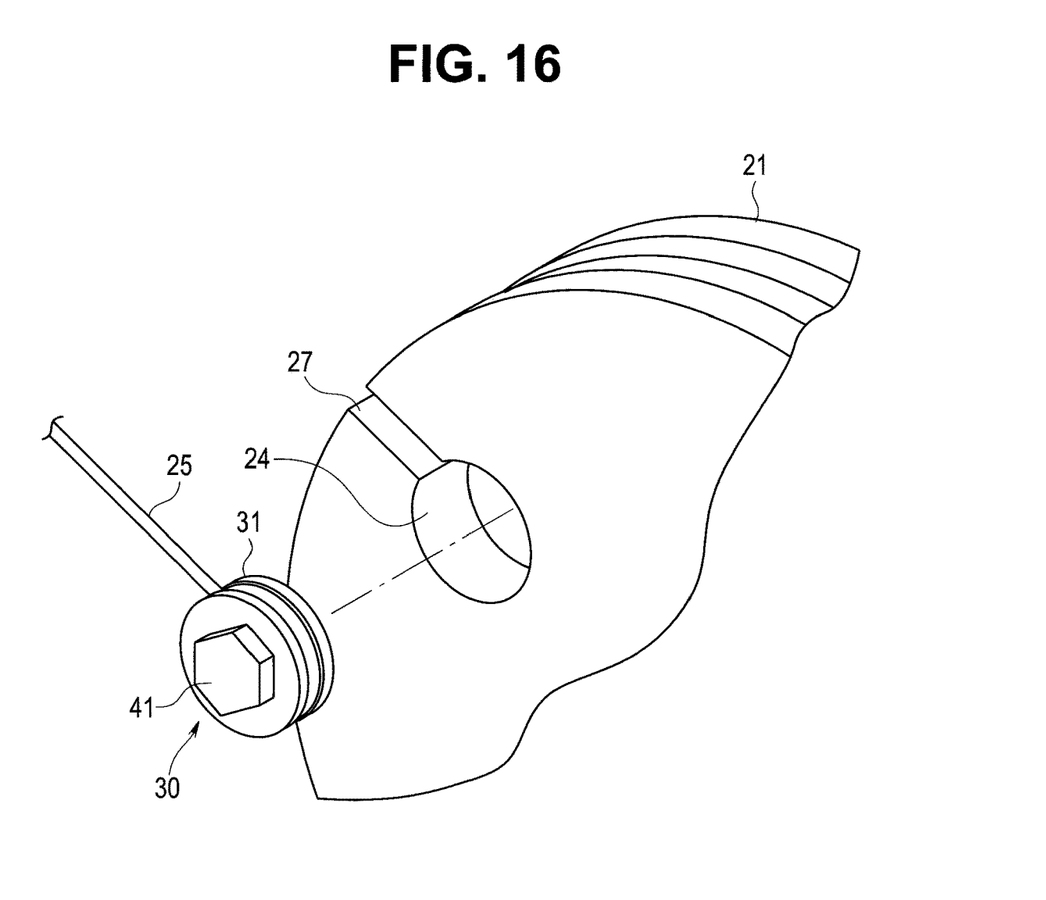
FIG. 16 is an exploded perspective view showing a state where a wire fixing structure according to a sixth modification is fixed to a pulley.

FIG. 16 is an exploded perspective view showing a state where a wire fixing structure according to a sixth modification is fixed to a pulley.

As shown in FIG. 16, with respect to the configuration for mounting a fixing member 31 of a wire fixing structure 30 to a pulley 21, in place of screw fixing, a circular columnar recessed portion 24 may be formed in the pulley 21, and the fixing member 31 may be mounted in the recessed portion 24 in an engaging manner.

The present invention is not limited to the above-mentioned embodiment, and it goes without saying that various modifications and applications can be carried out without departing from the gist of the present invention. Further, the above-mentioned embodiment includes the inventions in various stages, and various inventions can be extracted by suitably combining the plurality of disclosed constitutional element.

For example, the task to be solved by the invention can be overcome even when some constitutional elements are deleted from all constitutional elements disclosed in the embodiment. When advantageous effects of the present invention can be obtained, the configuration from which the constitutional elements are deleted can be extracted as the invention. Further, components in the embodiment and the modifications which differ from each other may be suitably combined. The present invention is not limited by the specific embodiment except the invention is restricted by attached claims.

The present invention can realize a wire fixing structure and an endoscope where a towing wire for bending a bending portion can be stably fixed to a pulley without causing slackening of the towing wire.

What is claimed is:

1. A wire fixing structure comprising:
   a pulley having an outer surface;
   a wire disposed on the outer surface and the wire configured to bend a bending portion of an endoscope;
   a wire fixing body formed separately from the pulley, the wire fixing body configured to be fixed to the pulley, the wire fixing body comprising:
   a first hole accommodating first and third portions of the wire, wherein a second portion of the wire is between the first and third portions and not disposed in the first hole; and
   a second hole communicating and intersecting with the first hole; and
   a fastener inserted into the second hole, wherein
   the fastener is configured to press and fix the first portion and the third portion in the first hole.

2. The wire fixing structure according to claim 1, wherein the wire fixing body further comprising an outer periphery upon which the second portion of the wire is wound.

3. The wire fixing structure according to claim 2, wherein the wire further includes:
   a fourth portion extending from the third portion and disposed out from the first hole, the fourth portion being wound around the outer periphery; and
   a fifth portion extending from the fourth portion and disposed in the first hole,
   wherein the fastener further presses and fixes the fifth portion in the first hole.

4. The wire fixing structure according to claim 2, wherein the outer periphery of the wire fixing body has a circular shape.

5. The wire fixing structure according to claim 2, wherein the outer periphery of the wire fixing body has a non-circular shape.

6. The wire fixing structure according to claim 5, wherein the non-circular shape of the outer periphery of the wire fixing body is a polygonal shape.

7. The wire fixing structure according to claim 2, wherein the outer periphery of the wire fixing body is a wire fixing body groove formed on the outer periphery.

8. The wire fixing structure according to claim 7, wherein the wire fixing body groove includes a first groove portion and a second groove portion separated by the first hole, the second portion of the wire being wound around at least one of the first groove portion of the second groove portion.

9. The wire fixing structure according to claim 8, wherein the second portion of the wire is wound around each of the first groove portion and the second groove portion.

10. The wire fixing structure according to claim 2, wherein the second portion of the wire is folded outside the outer periphery of the wire fixing body.

11. The wire fixing structure according to claim 1, wherein the second hole is a female threaded hole, and the fastener comprises a male threaded member threadedly engaging with the female threaded hole.

12. The wire fixing structure according to claim 1, wherein the wire fixing body is fixed on a side surface of the pulley, the side surface intersecting a turning shaft of the pulley.

13. The wire fixing structure according to claim 12, wherein
   the pulley comprising a plurality of threaded holes on the side surface; and
   the wire fixing body includes a plurality of through holes respectively corresponding to the plurality of threaded holes;

the wire fixing structure further comprises a wire fixing body fastener disposed in each of the plurality of through holes and engaged with each corresponding threaded hole to fix the wire fixing body to the side surface of the pulley.

14. The wire fixing structure according to claim 12, wherein the side surface of the pulley further comprises a recess, the wire fixing body being disposed within the recess.

15. The wire fixing structure according to claim 1, wherein the fastener is inserted into the second hole in a direction intersecting a plan in which the first portion of the wire and the third portion of the wire are aligned.

16. The wire fixing structure according to claim 1, wherein the outer surface of the pulley comprises a pulley groove, the pulley having a cutout in a wall of the pulley groove, the wire extending from the pulley groove, through the cutout and to the wire fixing body.

17. The wire fixing structure according to claim 1, further comprising at least two anchors disposed in the first hole;
   wherein a first of the at least two anchors including:
      a first concave portion configured to accommodate the first portion of the wire; and
      a plurality of first convex portions; and
   a second of the at least two anchors including:
      a second concave portion configured to accommodate the third portion of the wire; and
      a plurality of second convex portions configured to mesh with the plurality of first convex portions.

18. An endoscope comprising the wire fixing structure according to claim 1.

19. A wire fixing structure comprising:
   a wire configured to bend a bending portion of an endoscope;
   a wire fixing body configured to be fixed to a pulley, the wire fixing body comprising:
      a first hole accommodating first and third portions of the wire, wherein a second portion of the wire is between the first and third portions and not disposed in the first hole; and
      a second hold communicating and intersecting with the first hole; and
   a fastener inserted into the second hole;
   wherein the fastener is configured to press and fix the first portion and the third portion in the first hole; and
   the fastener is inserted into the second hole in a direction intersecting a plane in which the first portion of the wire and the third portion of the wire are aligned.

20. A wire fixing structure comprising:
   a wire configured to bend a bending portion of an endoscope;
   a wire fixing body configured to be fixed to a pulley, the wire fixing body comprising:
      a first hole accommodating first and third portions of the wire, wherein a second portion of the wire is between the first and third portions and not disposed in the first hole;
      a second hole communicating and intersecting with the first hole; and
      a groove formed on an outer periphery of the wire fixing body, the second portion of the wire being disposed in the groove; and
   a fastener inserted into the second hole;
   wherein the fastener is configured to press and fix the first portion and the third portion in the first hole.

* * * * *